US00PP22598P3

(12) United States Plant Patent
Morgan

(10) Patent No.: US PP22,598 P3
(45) Date of Patent: Mar. 20, 2012

(54) *BEGONIA* PLANT NAMED 'NZCFOUR'

(50) Latin Name: *Begonia boliviensis×micranthera*
Varietal Denomination: Nzcfour

(75) Inventor: Ed Morgan, Auckland (NZ)

(73) Assignee: New Zealand Institute for Plant and Food Research, Ltd., Palmerston North (NZ)

( * ) Notice: Subject to any disclaimer, the term of this patent is extended or adjusted under 35 U.S.C. 154(b) by 0 days.

(21) Appl. No.: 12/803,896

(22) Filed: Jul. 9, 2010

(65) Prior Publication Data

US 2012/0011629 P1 Jan. 12, 2012

(51) Int. Cl.
*A01H 5/00* (2006.01)

(52) U.S. Cl. ..... Plt./343

(58) Field of Classification Search ..... Plt./343, Plt./349

See application file for complete search history.

*Primary Examiner* — June Hwu
*Assistant Examiner* — Louanne Krawczewicz Myers
(74) *Attorney, Agent, or Firm* — Cassandra Bright

(57) ABSTRACT

A new and distinct *Begonia* cultivar named 'Nzcfour' is disclosed, characterized by its unique foliage and stem coloration. The new cultivar is a *Begonia,* typically suited for garden and ornamental container use.

1 Drawing Sheet

Figure 1:
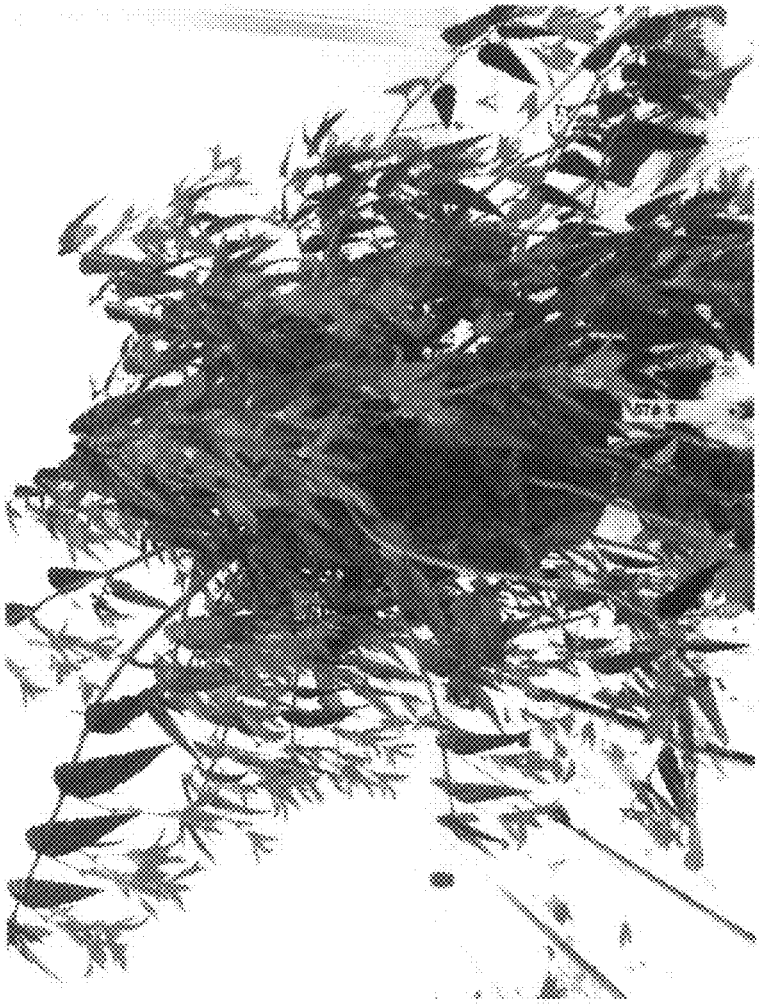

Latin name of the genus and species: *Begonia boliviensis× micranthera.*
Variety denomination: 'Nzcfour'.

BACKGROUND OF THE INVENTION

The new cultivar is a product of a planned breeding program. The new variety originated from a cross pollination of the seed parent, an unpatented, variety of *Begonia boliviensis×micranthera* with the pollen parent, an unpatented variety of *Begonia boliviensis* directed by the inventor in February of 2007. The crossing was made in Palmerston North, New Zealand, at a commercial greenhouse.

'Nzcfour' was selected by the inventor, Ed Morgan in August 2007 in Palmerston, New Zealand at a commercial greenhouse among seedlings resulting from the February 2007 crossing.

After selection of the new cultivar, asexual reproduction of 'Nzcfour' was first performed in the same commercial greenhouse by vegetative cuttings in December of 2007. 'Nzcfour' has since produced several generations and has shown that the unique features of this cultivar are stable and reproduced true to type.

SUMMARY OF THE INVENTION

The cultivar 'Nzcfour' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Nzcfour.' These characteristics in combination distinguish 'Nzcfour' as a new and distinct *Begonia* cultivar.

1. Distinctive Greyed-Purple color of underside of foliage.
2. Unusual bronze/purple colored stems.

PARENTAL COMPARISON

Plants of the new cultivar 'Nzcfour' are similar to the female parent in most horticultural characteristics. However, 'Nzcfour' differs in producing different colored flowers.

Plants of the new cultivar 'Nzcfour' are similar to the male parent in most horticultural characteristics. However, 'Nzcfour' differs in producing foliage of a different color.

COMMERCIAL COMPARISON

Plants of the new cultivar 'Nzcfour' are similar to the commercial variety 'NZCTWO' U.S. Plant Pat. No. 21,177 in most horticultural characteristics. However, 'Nzcfour' differs in producing different color flowers than, 'NZCTWO' and darker stems.

BRIEF DESCRIPTION OF THE PHOTOGRAPH

The accompanying photograph in FIG. 1 illustrates in full color a typical plant of 'Nzcfour' grown in a greenhouse in Palmerston North, New Zealand. This plant is approximately 2 years old, shown in a 2 liter pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'Nzcfour' plants grown in a greenhouse in Stuttgart, Germany. Temperatures ranged from 16° C. to 20° C. at night to 18° C. to 20° C. during the day. No artificial light, photoperiodic treatments or chemical treatments were given to the plants. Measurements and numerical values represent averages of typical plant types.

Botanical classification: *Begonia boliviensis×micranthera* 'Nzcfour'

Age the plant described: Approximately 1 year.

Container size of the plant described: 3 liter commercial container.

PROPAGATION

Typically reproduced by vegetative cuttings. Under ideal greenhouse conditions, at temperatures from 16° to 20° C. a fully rooted plant, ready to be planted outdoors is produced in 9 weeks time. Tuber formation not observed to date.

PLANT

Growth habit: Upright. Basal shoots arising vertically.
Mature height: Approximately 80 cm.
Plant spread: Approximately 45 cm.
Growth rate: Moderate.
Branching characteristics: Basal branching.
Internode length: Average 90 cm.
Stem diameter: Approximately 1.2 cm.
Stem texture: Smooth.
Stem color: Near RHS Greyed-Purple 183D.
Length: Approximately 60 cm

FOLIAGE

Leaf:
- *Arrangement.*—Alternate and opposite occurring leaves occurring at 90 degree angle from stem.
- *Quantity.*—Average 10 per primary branches 3 to 6 on shorter branches.
- *Average length.*—Broad apical section 6.6 cm average, narrow basal section 2.2 cm average.
- *Average width.*—Broader section 2.9 cm, narrower section 1.1 cm.
- *Shape of blade.*—curved, non-symmetrical lanceolate.
- *Apex.*—Acute.
- *Base.*—Oblique.
- *Margin.*—Double serrate.
- *Texture upper and lower surface.*—Pubescent.
- *Aspect.*—Slight convex curve.
- *Color.*—Young foliage upper side: Near RHS Yellow-Green 147A. Young foliage under side: Near RHS Greyed-Purple 185A. Mature foliage upper side: RHS Yellow-Green 147A. Margins near Greyed-Purple 183B. Mature foliage under side: RHS Greyed-Purple 183B.
- *Venation.*—Type: Pinnate. Venation color upper side: RHS Green 139B. Venation color under side: RHS Greyed-Purple 183B.
- *Petiole.*—Length: Approximately 0.5 to 1.0 cm. Diameter: Approximately 0.2 cm. Color: Near RHS Greyed-Purple 183C. Texture: Smooth.
- *Stipule.*—Not observed to date.

FLOWER

Natural bloom season: Spring until Fall.
Flower arrangement: Singly occurring, stellate shaped. Self-cleaning flowers last approximately 5 days on the plant. At present, only one type of flower has been observed to date.
Bud:
- *Shape.*—Ovate.
- *Length.*—Approximately 1 to 2 cm.
- *Diameter.*—Approximately 0.5 to 1.0 cm.
- *Color.*—Near RHS Red 45C and 45D, both colors present.

Flower size:
- *Average diameter.*—2.7 cm.
- *Depth.*—Average 3.1 cm.

Tepals:
- *Quantity.*—4, 2 larger tepals, 2 smaller tepals.
- *Larger tepals.*—Length: Approximately 2.4 cm. Width: Approximately 1.3 cm.
- *Smaller tepals: Length: Approximately* 2.3 cm. Width: Approximately 0.7 cm.
- *Arrangement.*—Overlap at base for lower ⅓ of flowers.
- *Shape.*—Very narrow deltoid.
- *Apex.*—Acute.
- *Base.*—Obtuse.
- *Margin.*—Entire.
- *Texture, upper and lower surfaces.*—Smooth.
- *Color.*—Outside tepals when opening: Near RHS Red 52A. Inner tepals when opening: Near RHS Red 45C and Red 47B, both colors present. Outside tepals: Near RHS Red 43B. Inner tepals: Near RHS Red 52A.

Sepals: Not Present.
Pedicels:
- *Length.*—Approximately 0.23 cm.
- *Diameter.*—Approximately 0.15 cm.
- *Angle.*—About 70° to the lateral branch.
- *Texture.*—Smooth.
- *Color.*—Near RHS Red 45A and also Greyed-Red 179A.
- *Bracteoles.*—Length: Approximately 0.2 cm. Diameter: Approximately 0.2 cm. Shape: Deltoid. Texture: Smooth. Color: Near RHS Red 43C with Greyed-Red 179A.

Peduncles:
- *Length.*—Approximately 4 cm.
- *Diameter.*—Approximately 0.3 cm.
- *Angle.*—About 70° to the lateral branch.
- *Texture.*—Smooth.
- *Color.*—Near RHS Red 45A and also Greyed-Red 179A.
- *Peducle bracts.*—Color: Near RHS Red 43C. Texture: Smooth. Shape: Deltoid. Size: Approximately 0.3 cm in diameter and length.

Fragrance: None.

REPRODUCTIVE ORGANS

Stamens:
- *Number.*—Approximately 30.
- *Stamen length.*—Approximately 0.2 cm.
- *Stamen color.*—Near RHS Yellow-Orange 14C.
- *Filament color.*—Near RHS Yellow-Orange 14C.
- *Anther color.*—Near RHS Yellow-Orange 17C.
- *Anther shape.*—Linear.
- *Anther length.*—Approximately 0.1 cm.
- *Pollen.*—Moderate, colored near RHS Yellow-Orange 14C.

Pistil: 6 present.
- *Pistil color.*—Near RHS Orange 25B.
- *Pistil length.*—Approximately 8 cm.
- *Stigma color.*—Near RHS Orange 26B.
- *Style color.*—Near RHS Orange 27D.

OTHER CHARACTERISTICS

Seeds: Typical dust-like *Begonia boliviensis* seeds. Colored near Green 137A and Red 52C.
Disease/pest resistance: Moderate resistance and susceptibility to common diseases and pests of *Begonia* have been observed in the new variety.
Temperature tolerance: Tolerates temperatures from approximately 4° C. to 38° C.

What is claimed is:

1. A new and distinct cultivar of *Begonia boliviensis×micranthera* plant named 'Nzcfour' as herein illustrated and described.

* * * * *